(12) United States Patent
Labruzzo

(10) Patent No.: US 12,201,729 B2
(45) Date of Patent: *Jan. 21, 2025

(54) PROCESS FOR MESALAZINE SOLID FORMULATIONS

(71) Applicant: ALFASIGMA S.P.A., Bologna (IT)

(72) Inventor: Carla Labruzzo, Milan (IT)

(73) Assignee: ALFASIGMA S.P.A., Bologna (IT)

( * ) Notice: Subject to any disclaimer, the term of this patent is extended or adjusted under 35 U.S.C. 154(b) by 109 days.

This patent is subject to a terminal disclaimer.

(21) Appl. No.: 18/047,964

(22) Filed: Oct. 19, 2022

(65) Prior Publication Data

US 2023/0104254 A1    Apr. 6, 2023

Related U.S. Application Data

(62) Division of application No. 16/091,397, filed as application No. PCT/IB2017/051907 on Apr. 4, 2017, now Pat. No. 11,504,331.

(30) Foreign Application Priority Data

Apr. 5, 2016 (IT) .................. 102016000034518

(51) Int. Cl.
| | |
|---|---|
| A61K 9/16 | (2006.01) |
| A61K 9/20 | (2006.01) |
| A61K 9/28 | (2006.01) |
| A61K 31/606 | (2006.01) |

(52) U.S. Cl.
CPC .......... *A61K 9/1694* (2013.01); *A61K 9/1623* (2013.01); *A61K 9/1635* (2013.01); *A61K 9/1652* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2095* (2013.01); *A61K 9/2846* (2013.01); *A61K 31/606* (2013.01)

(58) Field of Classification Search
CPC .................................................. A61K 9/1694
See application file for complete search history.

(56) References Cited

U.S. PATENT DOCUMENTS

| | | | |
|---|---|---|---|
| 4,539,198 A | 9/1985 | Powell et al. | |
| 6,773,720 B1 | 8/2004 | Villa et al. | |
| 11,504,331 B2 | 11/2022 | LaBruzzo | |
| 2003/0138495 A1* | 7/2003 | Jepsen | A61K 9/2081 264/15 |
| 2009/0017110 A1 | 1/2009 | Cherukuri et al. | |
| 2009/0162434 A1 | 6/2009 | Ugwoke et al. | |
| 2013/0225539 A1 | 8/2013 | Gaab et al. | |
| 2018/0311155 A1* | 11/2018 | Wilhelm | A61P 1/00 |
| 2019/0105275 A1* | 4/2019 | Liang | A61K 9/2846 |
| 2019/0151245 A1 | 5/2019 | Labruzzo | |

FOREIGN PATENT DOCUMENTS

| | | | |
|---|---|---|---|
| EP | 1004297 | * | 5/2000 |
| WO | 98/26767 A2 | | 6/1998 |
| WO | 2012/028698 A1 | | 3/2012 |
| WO | WO 2015/193788 | * | 12/2015 |

OTHER PUBLICATIONS

Certification Statement and List—37 CFR 1.98(d)(1) filed in U.S. Appl. No. 18/047,964, filed Oct. 19, 2022 on behalf of Sofar S.P.A. 1 page.
Examination Report No. 1 for standard patent application for Australian Application No. 2017247783 filed on Apr. 4, 2017 on behalf of Sofar S.p.A. Mailed on Jan. 12, 2022. 4 pages.
Examination Report No. 2 for standard patent application for Australian Application No. 2017247783 filed on Apr. 4, 2017 on behalf of Sofar S.p.A. Mailed on Nov. 25, 2022. 2 pages.
First Examination Report for Mexican Application No. MX20180011685 filed on Apr. 4, 2017 on behalf of Sofar S.p.A. Mailed on May 13, 2021. 8 pages. Original and English translation.
"Lialda™ (mesalamine) Delayed Release Tablets, Patient Information Leaflet", Shire US Inc, (2007), pp. 1-8, XP093028338.
Remington, The Science & Practice of Pharmacy, 22nd Edition (2013) by the University of the Sciences in Philadelphia. pp. 338 and 967. 4 pages.
Rowe R.C. et al., "Handbook of Pharmaceutical Excipients" Pharmaceutical Press, 5th Edition, (2006), 945 pages.

* cited by examiner

*Primary Examiner* — Genevieve S Alley
(74) *Attorney, Agent, or Firm* — Steinfl + Bruno, LLP

(57) ABSTRACT

The present invention relates to a process to prepare solid pharmaceutical forms comprising a quantity of mesalazine comprised between 75 and 95%, i.e. between 1000 and 1600 mg of drug per dosage unit. Furthermore, the present invention relates to a granulate and/or tablets obtained/obtainable with the process according to the invention, preferably coated to allow the con-trolled release of the drug. Finally, the present invention relates to the use of the granulate and/or the tablets as a medicament, preferably for the treatment of chronic inflammatory pathologies that preferably affect the intestinal tract.

20 Claims, No Drawings

PROCESS FOR MESALAZINE SOLID FORMULATIONS

CROSS REFERENCE TO RELATED APPLICATIONS

The present application is a divisional application of U.S. application Ser. No. 16/091,397 filed on Oct. 4, 2018, which is the U.S. national stage of International Application PCT/IB2017/051907, filed Apr. 4, 2017, which claims priority to Italian Patent Application No. 102016000034518, filed Apr. 5, 2016, all of which are incorporated herein by reference in their entirety.

DESCRIPTION

The present invention relates to a process to prepare solid pharmaceutical forms comprising a quantity of mesalazine comprised between 75 and 95%, i.e. between 1000 and 1600 mg of drug per dosage unit.

Furthermore, the present invention relates to a granulate and/or tablets obtained/obtainable with the process according to the invention, preferably coated to allow the controlled release of the drug.

Finally, the present invention relates to the use of the granulate and/or tablets as a medicament, preferably for the treatment of chronic inflammatory pathologies, preferably affecting the intestine.

BACKGROUND

Various studies regarding patient behaviour indicate that only half of patients leaving a medical practice with a pharmaceutical prescription take the drug in compliance with the physician's instructions.

Adherence to pharmaceutical prescriptions, commonly indicated by the term compliance, is generally defined as the tendency of a patient to take the drugs in accordance with the physician's prescription. In particular, the compliance percentage is determined as the percentage of the prescribed doses actually taken by the patient in a certain period of time.

The most likely consequence of lack of compliance is that the disease cannot be improved and/or treated. It follows that the patient's quality of life worsens and the same can be said for the cost of health care.

Cases of lack of compliance associated with complex therapy and dosing regimens are particularly frequent, as in the cases of subjects affected by a chronic condition. In fact, the non-compliance of patients to therapy regimens in the case of chronic diseases is now largely documented and confirmed by the recurrence of symptoms, in particular, in patients affected by chronic inflammatory intestinal pathologies, such as ulcerous colitis and Crohn's disease. In fact, these patients are forced to take repeated doses of the drug in order to reach the effective daily dose of therapy. This demanding therapy regimen is connected with the formulation techniques currently available for these drugs which do not allow the introduction of high amounts of the active ingredient in the individual formulations.

Mesalazine or 5-aminosalicylic acid (5-ASA) is an example of this type of drug. It is a molecule with anti-inflammatory activity, widely used for treating chronic inflammatory pathologies of the intestinal tract.

Mesalazine is normally administered orally or rectally. Oral pharmaceutical formulations currently available on the market allow the active ingredient to pass through the stomach, and often also the small intestine, so as to release the drug in a site-specific way at the site of the inflammation, where it can act topically in direct contact with the mucosa.

To obtain site-specificity and topical effectiveness, solid pharmaceutical formulations of mesalazine are usually coated by one or more layers that allow its controlled release.

It is extremely important to guarantee the maximum patient compliance to treatment with mesalazine since, for example, patients with ulcerous colitis who do not adhere to therapy have a risk of relapse that is five times higher with respect to patients with greater compliance. Furthermore, as stated above, the continuation of the disease has a strong negative impact on the health and quality of life of patients and implies an increase in hospitalisations, medical appointments and pharmaceutical cost for the subsequent use of alternative therapies that are certainly more expensive and characterised by a worse tolerability profile (e.g. systemic steroids, immunosuppressants, biological drugs).

In light of the above, there is a strongly felt need to develop a method that allows to prepare solid pharmaceutical formulations with a high active ingredient content and that simultaneously allows to maintain the critical characteristics of a solid pharmaceutical formulation, in particular, friability, hardness, disintegration and weight uniformity, especially in relation to the subsequent coating step of the formulation. In the case of mesalazine this allows the patient to be provided with a solid pharmaceutical formulation with a high active ingredient content and therefore with the possibility to take the drug a limited number of times if not once a day. Therefore, the patient manages to comply better with the therapeutic treatment and therefore to be treated, improves his/her state of health and relieve the health system of the high costs associated with poor compliance.

The applicant has found an answer to the above needs with a process according to the appended claims that allows to prepare solid pharmaceutical formulations (forms) with a quantity of mesalazine comprised between 75 and 95%, i.e. between 1000 and 1600 mg of drug per dosage unit.

The present invention will be described in detail below, also with reference to the following definitions that complete it and will be illustrated by way of non-limiting example.

Definitions

Within the context of the present invention mesalazine means 5-amino-2-hydroxybenzoic acid, or 5-aminosalicylic acid or 5-ASA and/or salts thereof and/or derivatives thereof, preferably esters, possibly conjugated and/or chemically modified.

Preferably mesalazine as a pharmaceutically active ingredient has at least one of the following characteristics:
  apparent density ranging from 0.15 to 0.35 g/ml, preferably from 0.2 to 0.3 g/ml, where apparent density means the density of a powder as poured, measured in g/ml; and/or
  packing density ≥0.4 g/ml, where packing density means the density of a powder subjected to packing through a specific test and is measured in g/ml; and/or
  Particle Size Distribution (PSD) for 100% of the particles ≤90 μm (micron), preferably ≤70 μm; of which:
    D90 comprised between 30 and 45 μm, preferably between 35 and 40 μm; and/or
    D50 comprised between 5 and 20 μm, preferably between 10 and 15 μm.
  Where particle size distribution means the distribution on a statistical basis of the size of a powder/granulate measured in μm; D90 means the dimensional value below which 90% of the population is found; D50 means the dimensional value below which 50% of the population is found.

Within the context of the present invention, solid gastro-resistant formulation means a solid oral pharmaceutical form able to pass through the gastric tract still intact, so as not to release the drug contained therein into the stomach/duodenum, for the purpose of protecting the molecule, specifically the active ingredient mesalazine, from the gastric environment and preventing it from being absorbed.

Within the context of the present invention, modified-release solid formulation means a pharmaceutical form in which the liberation profile of the active ingredient is determined by the pharmaceutical formulation.

Within the context of the present invention, granulate means the result of the transformation of powder particles into solid aggregates having their own resistance and porosity characteristics. In particular, in this context, this constitutes the intermediate step for the preparation of tablets, sachets, capsules and extemporaneous preparations of liquid forms.

Preferably, in this context, the granulate has at least one of the following characteristics:
  mean density of granulate ranging from 0.65 to 0.85 g/ml; and/or
  particle size for 100%≤1.5 mm.

Within the context of the present invention, hardness means the resistance of the tablet to breaking, measured as a force: N, Kp etc.

Within the context of the present invention, friability means the resistance of the tablets to mechanical stress, measured as percentage weight loss after the conventional test.

Within the context of the present invention, disintegration means the time necessary for the tablets to break down, measured in minutes with the conventional test.

DETAILED DESCRIPTION

The present invention relates to a process for the preparation of a solid pharmaceutical formulation comprising 70-95%, preferably 80-90% of mesalazine and/or a salt thereof and/or a derivative thereof, preferably for oral use, said process comprising the steps of:
  (i) preparing a powder bed comprising mesalazine and/or a salt thereof and/or a derivative thereof and possibly also at least one pharmacologically acceptable excipient;
  (ii) adding to the powder according to step (i) an aqueous solution comprising 10-20% of a binding agent, preferably polyvinylpyrrolidone, so as to obtain a granulate, said granulate being characterised by a moisture content ranging from 20 to 40%;
  (iii) drying the granulate obtained from step (ii) until reaching a moisture content lower than or equal to 3.0%, preferably comprised between 2.5 and 3.0%;
  (iv) mixing the granulate dried according to step (iii) with at least one disintegrating agent;
  (v) adding water to the granulate obtained from step (iv) until reaching a moisture content ranging from 3.0 to 3.5%; and
  (vi) compacting the granulate, preferably after having added at least one lubricant agent.

Preferably in step (i) the excipients are at least one diluent agent and/or a disintegrating agent.

The diluent agents according to the present invention are preferably selected from among: cellulose, polyols, starch derivatives and mixtures thereof. More preferably, said diluents are selected from among: mannitol, starch, corn starch, microcrystalline cellulose, maltodextrin and mixtures thereof.

The disintegrating agents according to the present invention are preferably selected from among: starch derivatives, cellulose and polyvinylpyrrolidone derivatives, preferably sodium carboxymethyl starch, croscarmellose sodium, crospovidone, modified starch and pregelatinized starch.

The binding agents according to the present invention are preferably selected from among: polyvinylpyrrolidone, povidone, preferably PVP K30, and cellulose derivatives, preferably: hydroxypropyl methylcellulose, hydroxypropyl cellulose, carboxymethylcellulose or a mixture thereof.

The aqueous solution of binding agent is preferably added through a nozzle, which may be pressurized or not, and is preferably supplied by a peristaltic pump. The solution is added to the powder bed and subsequently further water can be added until an effort of the mixer blade preferably ranging from 1000 to 1800 Nm and/or a water level in the powder mixture preferably ranging from 30% to 40% is reached.

The drying according to step (iii) is preferably carried out in a vacuum or ventilated static oven, or in a fluid bed.

The temperature of the drying step preferably ranges from 45 to 70° C. for the oven, whereas the incoming air in the case of the fluid bed has a temperature that preferably ranges from 65 to 85° C., more preferably from 70 to 80° C.

After drying a disintegrating agent is preferably added to the granulate.

The disintegrating agents are preferably those described above.

The compacting according to step (vi) preferably takes place by applying a force comprised between 30 and 50 KN.

The lubricant agents according to the present invention are preferably selected from among: anhydrous colloidal silica, talc, magnesium stearate, glyceryl behenate, sodium stearyl fumarate and mixtures thereof.

Following the compacting step, it is possible to calibrate the granulate, preferably using a metal mesh characterized by mesh sizes that preferably range from 0.85 to 1.5 mm. Finally, the granulate, preferably calibrated, is mixed with at least one lubricant and/or glidant agent.

Steps (i)-(iii) define a step of the process also known as wet granulation.

Steps (iv) and (v) define a step of the process also known as granulate rewetting step.

In the last step (vi) the granulate is compacted and this step is also known as dry granulation.

Preferably, the apparent density of the granulate obtained/obtainable with the process according to the invention ranges on average from 0.60 to 0.75 g/ml, more preferably from 0.65 to 0.75 g/ml.

Preferably, the packing density of the granulate obtained/obtainable with the process according to the invention ranges on average from 0.70 to 0.85 g/ml, more preferably from 0.75 to 0.85 g/ml.

Preferably the average size of the granulate obtained/obtainable with the process according to the invention is for 100% of the particles lower than or equal to 1.5 mm.

In some preferred embodiments of the invention, the granulate obtained/obtainable from the process described above is further processed for the purpose of obtaining a further solid pharmaceutical form, preferably tablets, also characterised by 70-95%, preferably 80-90%, of mesalazine and/or a salt thereof and/or a derivative thereof. Therefore, in the tablets the quantity of mesalazine (active ingredient) preferably ranges from 1000 to 1600 mg.

Preferably, the tablets according to the present invention while having a high concentration of mesalazine (active ingredient) are characterized by physical parameters, in particular friability, hardness, disintegration and weight uniformity, which are suitable and optimal for allowing a subsequent coating step to enable the controlled release of this drug.

With the formulation processes currently available, it is not possible to obtain the same result, maintaining a release of the drug that is simultaneously complete and immediate so that it can perform its topical action.

Preferably the tablets obtained with the process according to the present invention are characterized by friability ranging from 0.000% to 1.000%, more preferably ranging from 0.000% to 0.250%.

Preferably the tablets obtained with the process according to the present invention are characterized by hardness preferably higher than 6 Kp, more preferably comprised between 10Kp and 30Kp.

Preferably the tablets obtained with the process according to the present invention are characterised by disintegration in less than 15 minutes.

Preferably the tablets obtained with the process according to the present invention comprise at least one coating (coat, layer, film) for the controlled release of the drug.

The methods and substances used to coat the tablets are those known in the prior art. Preferably the coating is a pH-dependent coating that preferably comprises at least one of the following compounds: polymers and copolymers of methacrylic acid, plasticizing agents, pigments and glidant agents. In a preferred embodiment of the invention the mesalazine used has the following characteristics:
- apparent density ranging from 0.15 to 0.35 g/ml, preferably from 0.20 to 0.30 g/ml, where apparent density means the density of a powder as poured, measured in g/ml; and/or
- packing density ≥0.4 g/ml, where packing density means the density of a powder subjected to packing through a specific test and is measured in g/ml; and/or
- particle size distribution (PSD) for 100% of the particles ≤90 μm, preferably ≤70 μm; of which:
  D90 comprised between 30 and 45 μm, preferably between 35 and 40 μm; and/or
  D50 comprised between 5 and 20 μm, preferably between 10 and 15 μm.

Where particle size distribution means the distribution on a statistical basis of the size of a powder/granulate measured in μm; D90 means the dimensional value below which 90% of the population is found; D50 means the dimensional value below which 50% of the population is found.

A further aspect of the present invention relates to a granulate obtained/obtainable with the process described above. Said granulate is preferably characterized by a quantity of mesalazine and/or a salt thereof and/or a derivative thereof ranging from 70 to 95%, preferably from 80 to 90%, and/or an average density ranging from 0.65 to 0.85 g/ml, of which preferably the apparent density ranges from 0.60 to 0.75 and/or more preferably from 0.65 to 0.75 g/ml and the packing density ranges on average from 0.70 to 0.85 g/ml, more preferably 0.75 to 0.85 g/ml and/or with an average size for 100% lower than or equal to 1.5 mm.

A further aspect of the present invention relates to the tablets obtained/obtainable through the process described above characterized by a quantity of mesalazine and/or a salt thereof and/or a derivative thereof ranging from 70 to 95%, preferably from 80 to 90% i.e. from 1000 to 1600 mg and preferably by at least one of the following physical parameters:
- friability preferably ranging from 0.000% to 1.000%, more preferably ranging from 0.000% to 0.250%; and/or
- hardness preferably higher than 6 Kp, more preferably comprised from 10 Kp to 30 Kp; and/or
- disintegration preferably less than 15 minutes.

Preferably the tablets are gastro-resistant and/or modified release tablets.

A further aspect of the invention relates to the granulate and/or the tablets described above or a process for producing a medicament, preferably for use in the treatment of an inflammation-based pathology, more preferably of the chronic type.

The chronic inflammatory pathologies to which the present invention refers are preferably those affecting the intestinal tract, more preferably ulcerous colitis and Crohn's disease.

Treatment is preferably by topical use. Administration is preferably oral.

EXAMPLE

The process according to the present invention was used by way of example for the preparation of solid pharmaceutical formulations with a high content of mesalazine as the active ingredient, in particular in quantities of 1200 mg/tablet.

The first step involves the dry mixing of a composition comprising the ingredients in Table I:

TABLE I

|  | % |
|---|---|
| Mesalazine | 83.33 |
| Microcrystalline cellulose | 2.85 |
| Sodium starch glycolate | 2.50 |
| Corn starch | 2.08 |
| Mannitol | 1.56 |

In particular, in this embodiment the quantities specified in Table II were mixed.

TABLE II

| Amount | Kg |
|---|---|
| MESALAZINE | 200.00 |
| MICROCRYSTALLINE CELLULOSE | 6.85 |
| MANNITOL | 3.75 |
| SODIUM STARCH GLYCOLATE | 6.00 |
| STARCH | 5.00 |

Then, the process involves a wet granulation step. In this specific case, a High Shear Mixer was used.

Wet granulation consists in wetting the mixture of Table II in the form of a powder bed with an 11% polyvinylpyrrolidone K30 (PVPK30) aqueous solution supplied by a peristaltic pump which, in particular, works at the flow rate of 4 L/min.

In order to reach the granulation end point, more water is generally added.

Usually, the wet granulation end point is reached when the measured effort of the mixer blade is between 1000-1800 Nm and the water content is 30-40%.

This is followed by a drying step which takes place in a static oven, which may be ventilated or vacuum, at a temperature comprised between 55-60° C. This step may also be performed in a fluid bed.

The granulate is considered dry when the LOD—loss on drying—is less than or equal to 2.5-3.0%.

At this point of the process, the residual water content in the product is fundamental. In fact, it has been demonstrated that a relative humidity degree comprised between 2.5-3.5% allows performing the subsequent steps until compression, thus obtaining the desired characteristics of the cores.

Since it is difficult to control such parameter during drying, it is necessary to rewet the granulate for the purpose of complying with the limits specified above. Therefore, once the drying step has finished, a rewetting step is carried out.

In the case of the fluid bed, such step may take place in a continuous equipment, following the drying step.

A compacting step of the granulate previously mixed with a disintegrating agent and magnesium stearate is then performed, through a roller compactor by applying a pressure comprised between 35 and 45 kN.

Subsequently, downstream of this system there is an oscillating granulator that has the aim of calibrating the belt coming out from the rollers thus producing a granulate with dimensions of less than 1.5 mm.

A further mixing step with only magnesium stearate follows.

Finally, a rotary tablet press allows tablets of active ingredient to be obtained that may be coated so as to be gastro-resistant. Table III below shows the composition of the gastro-resistant mesalazine tablets obtained with the process according to the present invention.

TABLE III

| CORE COMPONENTS | mg/tablet |
| --- | --- |
| MESALAZINE | 1200.00 |
| MICROCRYSTALLINE CELLULOSE 102 | 41.10 |
| CORN STARCH | 30.00 |
| MANNITOL | 22.50 |
| POLYVINYLPYRROLIDONE K30 | 45.00 |
| SODIUM CARBOXYMETHYL STARCH | 75.00 |
| MAGNESIUM STEARATE | 26.40 |
| FILM COMPONENTS | mg/tablet |
| METHACRYLIC ACID COPOLYMERS | 35.72 |
| TRIETHYL CITRATE | 17.89 |
| RED IRON OXIDE | 2.55 |
| TITANIUM DIOXIDE | 5.95 |
| TALC | 17.89 |

For the purpose of obtaining cores with a high drug load, the inventors have found the technical characteristics of the active ingredient used to be critical, in particular the following physical characteristics of mesalazine: PSD-particle size distribution, apparent and packing density were critical, in particular, for obtaining maximum reliability and repeatability of the process.

Preferably, the active ingredient, in the case of mesalazine, must have the characteristics summarized in Table IV.

TABLE IV

| PARAMETER | SPECIFICATIONS |
| --- | --- |
| APPARENT DENSITY-g/ml | 0.2-0.3 |
| PACKING DENSITY-g/ml | ≥0.4 |

TABLE IV-continued

| PARAMETER | SPECIFICATIONS |
| --- | --- |
| PSD-µm | 100% < 70 |
| D90-µm | 35-40 |
| D50-µm | 10-15 |

The invention claimed is:

1. A granulate obtained with a process for preparing a solid pharmaceutical formulation comprising based on a total weight of said solid pharmaceutical formulation from 70% to 95% by weight of mesalazine and/or a salt thereof and/or a derivative thereof, the process comprising steps in sequence of:
    preparing a powder bed comprising mesalazine and/or a salt thereof and/or a derivative thereof and optionally at least one pharmacologically acceptable excipient;
    adding to the powder bed an aqueous solution comprising from 10% to 20% of a binding agent so as to obtain a granulate of a mixture having a moisture content ranging from 20% to 40%;
    drying the granulate of the mixture until reaching a moisture content lower than or equal to 3.0%;
    mixing the granulate of the mixture with at least one disintegrating agent;
    adding water to the granulate of the mixture until reaching a moisture content ranging from 3.0% to 3.5%; and
    compacting the granulate of the mixture obtained by the adding water to the granulate of the mixture,
    wherein the granulate of the mixture comprises an amount of mesalazine and/or a salt thereof and/or a derivative thereof ranging based on a total weight of said solid pharmaceutical formulation from 70% to 95%, and/or an average density ranging from 0.60 to 0.85 g/ml, and/or a packing density ranging from 0.70 to 0.85 g/ml and/or an average size lower than 1.5 mm for 100% of granulate particles.

2. A tablet obtained by compressing the granulate according to claim 1, wherein the tablet comprises an amount of mesalazine and/or a salt thereof and/or a derivative thereof ranging based on a total weight of said solid pharmaceutical formulation from 70% to 95%, a weight from 1000 to 1600 mg, at least one physical parameter selected from the group consisting of a friability ranging from 0.000% to 1.000%, a hardness higher than 6 Kp, and a disintegration time of less than 15 minutes.

3. The tablet according to claim 2, further comprising at least one coating for gastro-resistance and/or for the controlled release of the drug.

4. The granulate according to claim 1, wherein the process further comprises adding at least one lubricating agent to the granulate of the mixture before compacting the granulate of the mixture.

5. The granulate according to claim 4, wherein said lubricating agent is selected from the group consisting of anhydrous colloidal silica, talc, magnesium stearate, glyceryl behenate, sodium stearyl fumarate and a mixture thereof.

6. The granulate according to claim 1, wherein the granulate of the mixture comprises an amount of mesalazine and/or a salt thereof and/or a derivative thereof ranging based on a total weight of said solid pharmaceutical formulation from 80% to 90%.

7. The granulate according to claim 1, wherein the drying the granulate of the mixture was performed until reaching a moisture content lower than or equal to 2.5%.

8. The granulate according to claim 7, wherein said metal mesh comprises a mesh size ranging from 0.85 mm to 1.5 mm.

9. The granulate according to claim 1, wherein said excipient is a diluent agent and/or a disintegrating agent, wherein said diluent agent is selected from the group consisting of cellulose, polyols, starch derivates and mixtures thereof and/or said disintegrating agent is selected from the group consisting of starch derivatives, cellulose and polyvinylpyrrolidone derivatives.

10. The granulate according to claim 1, wherein said excipient is a diluent agent and/or a disintegrating agent, wherein said diluent agent is selected from the group consisting of mannitol, starch, corn starch, microcrystalline cellulose, maltodextrin and mixtures thereof.

11. The granulate according to claim 1, wherein said excipient is a diluent agent and/or a disintegrating agent, said disintegrating agent is selected from the group consisting of sodium carboxymethyl starch, croscarmellose and crospovidone.

12. The granulate according to claim 1, wherein said binding agent is selected from the group consisting of polyvinylpyrrolidone and povidone.

13. The granulate according to claim 1, wherein said binding agent is selected from the group consisting of PVP K30 and cellulose derivatives.

14. The granulate according to claim 1, wherein said binding agent is selected from the group consisting of hydroxypropyl methylcellulose, hydroxypropyl cellulose, carboxymethylcellulose and a mixture thereof.

15. The granulate according to claim 1, wherein the drying is carried out in a vacuum or ventilated static oven, optionally at a temperature ranging from 45 to 70° C.

16. The granulate according to claim 1, wherein the drying is carried out in a fluid bed, optionally with incoming air ranging from 65 to 85° C. or from 70 to 80° C.

17. The granulate according to claim 1, wherein further comprising a step of calibrating the granulate, optionally with a metal mesh.

18. The granulate according to claim 1, wherein the mesalazine has at least one of the following characteristics:
  apparent density ranging from 0.15 to 0.35 g/ml, where apparent density means the density of a powder as poured;
  packing density ≥0.4 g/ml, where packing density means the density of a powder subjected to packing through a specific test;
  Particle Size Distribution (PSD) for 100% of the granulate particles ≤90 μm, where PSD means the distribution, on a statistical basis, of the particle size of a powder/granulate;
  D90, i.e. the size below which 90% of the population is found, comprised between 30 and 45 μm; and/or
  D50, i.e. the size below which 50% of the population is found, comprised between 5 and 20 μm.

19. A method for treatment of an inflammation-based pathology, the method comprising administering to a patient in need a tablet according to claim 2.

20. The method according to claim 19, wherein the inflammation-based pathology comprises a chronic type.

* * * * *